(12) United States Patent
Taylor et al.

(10) Patent No.: US 7,585,314 B2
(45) Date of Patent: Sep. 8, 2009

(54) DEVICE FOR INTERCONNECTING COMPONENTS IN SPINAL INSTRUMENTATION

(75) Inventors: Harold Taylor, Memphis, TN (US); Stewart Young, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 252 days.

(21) Appl. No.: 11/118,648

(22) Filed: Apr. 29, 2005

(65) Prior Publication Data

US 2006/0247626 A1    Nov. 2, 2006

(51) Int. Cl.
*A61B 17/70*    (2006.01)

(52) U.S. Cl. ...................................... 606/250

(58) Field of Classification Search ................... 606/54, 606/56, 57, 59, 61
See application file for complete search history.

(56) References Cited

U.S. PATENT DOCUMENTS

| | | | | |
|---|---|---|---|---|
| 4,471,159 | A | * | 9/1984 | Frank, Jr. .................. 174/94 R |
| 4,764,131 | A | * | 8/1988 | Beinhaur ..................... 439/781 |
| 5,047,029 | A | * | 9/1991 | Aebi et al. ..................... 606/61 |
| 5,154,719 | A | * | 10/1992 | Cotrel ........................... 606/73 |
| 5,312,405 | A | | 5/1994 | Korotko et al. |
| 5,330,473 | A | * | 7/1994 | Howland ...................... 606/61 |
| 5,476,462 | A | | 12/1995 | Allard et al. |
| 5,595,992 | A | | 1/1997 | Preuss et al. |
| 5,630,817 | A | | 5/1997 | Rokegem et al. |
| 5,702,393 | A | | 12/1997 | Pfaifer |
| 5,709,685 | A | | 1/1998 | Dombrowski et al. |
| 5,782,833 | A | * | 7/1998 | Haider .......................... 606/61 |
| 5,989,250 | A | | 11/1999 | Wagner et al. |
| 5,997,539 | A | | 12/1999 | Errico et al. |
| 6,110,172 | A | * | 8/2000 | Jackson ........................ 606/61 |
| 6,132,430 | A | | 10/2000 | Wagner |
| 6,171,311 | B1 | | 1/2001 | Richelsoph |
| 6,328,740 | B1 | | 12/2001 | Richelsoph |
| 6,328,741 | B1 | | 12/2001 | Richelsoph |
| 6,368,320 | B1 | | 4/2002 | Le Couedic et al. |
| 6,402,751 | B1 | | 6/2002 | Hoeck et al. |
| 6,416,040 | B1 | | 7/2002 | Bergman |
| 6,416,515 | B1 | | 7/2002 | Wagner |
| 6,562,040 | B1 | | 5/2003 | Wagner |
| 6,565,566 | B1 | | 5/2003 | Wagner et al. |
| 6,595,992 | B1 | | 7/2003 | Wagner et al. |
| 6,613,050 | B1 | | 9/2003 | Wagner et al. |
| 6,709,434 | B1 | * | 3/2004 | Gournay et al. ............... 606/61 |

(Continued)

FOREIGN PATENT DOCUMENTS

WO    WO 9909901 A1 *    3/1999

*Primary Examiner*—Thomas C Barrett
*Assistant Examiner*—Nicholas Woodall

(57) ABSTRACT

A device for connection to a component used in association with spinal instrumentation, including a connector body, at least one clamp element, and at least one fixation element. The connector body defines a receptacle extending therethrough and opening onto an outer surface thereof. The connector body also defines a passage in transverse communication with the receptacle. The clamp element includes at least two arm portions defining a space therebetween having an open end. The clamp element is positioned within the passage in the connector body with the space between the arm portions generally aligned with the receptacle and with the component received through the open end and retained within the space. The fixation element interacts with the clamp element to displace the clamp element relative to the connector body to position at least a portion of the component within the receptacle.

30 Claims, 6 Drawing Sheets

U.S. PATENT DOCUMENTS

| | | |
|---|---|---|
| 2002/0095153 A1 | 7/2002 | Jones et al. |
| 2003/0028192 A1 | 2/2003 | Schar et al. |
| 2004/0049188 A1 | 3/2004 | Slivka et al. |
| 2004/0230192 A1 | 11/2004 | Graf |
| 2004/0260285 A1 | 12/2004 | Steib et al. |

* cited by examiner

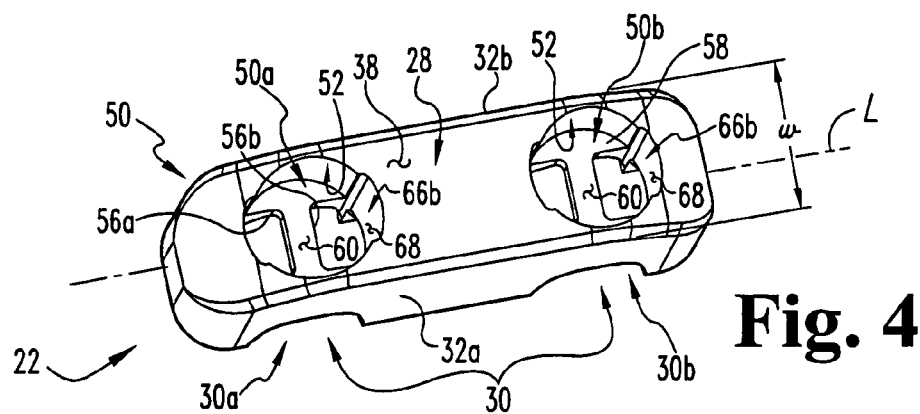
Fig. 4
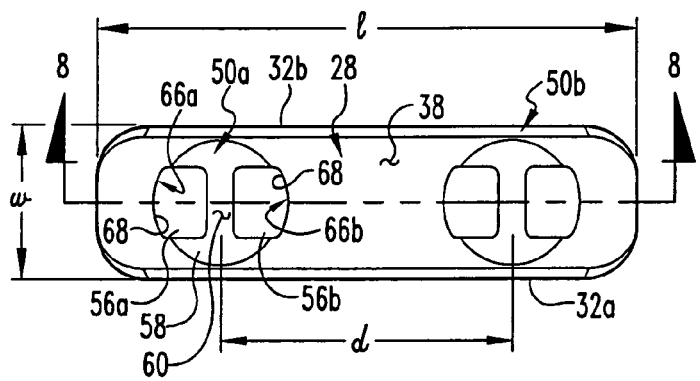
Fig. 6
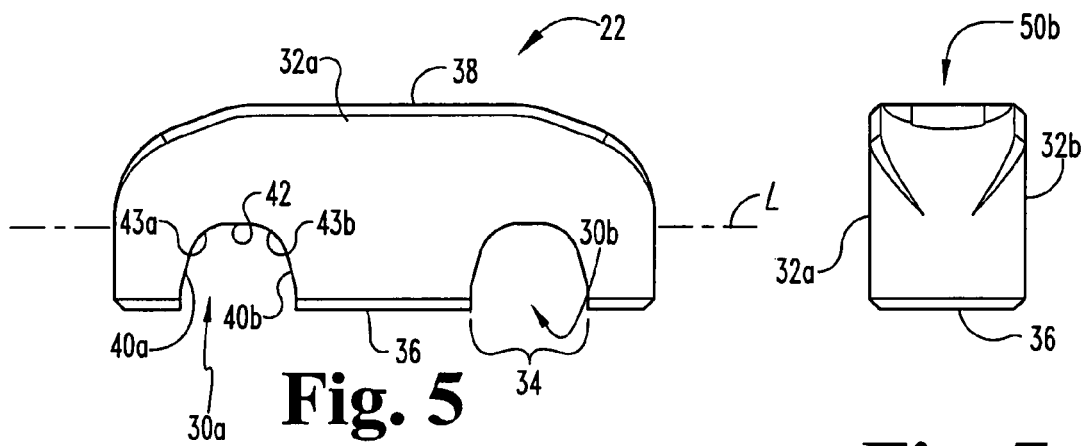
Fig. 5
Fig. 7
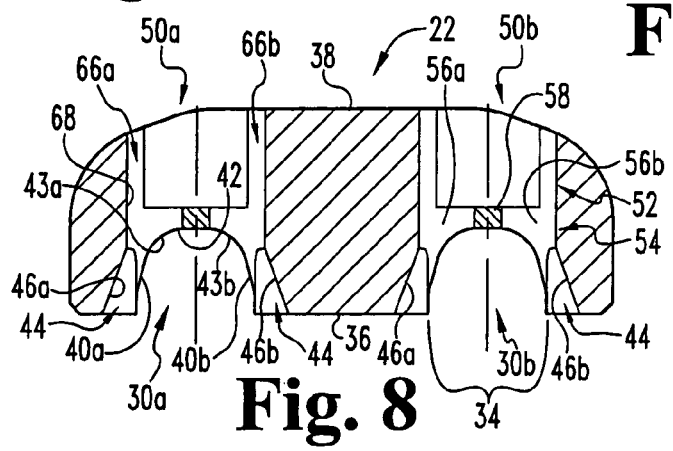
Fig. 8

DEVICE FOR INTERCONNECTING COMPONENTS IN SPINAL INSTRUMENTATION

FIELD OF THE INVENTION

The present invention relates generally to instrumentation for treatment of the spinal column, and more particularly relates to devices for interconnecting components in spinal instrumentation.

BACKGROUND

Several techniques and systems have been developed for use in treatment of the spinal column, and more specifically for stabilizing and supporting portions of the spinal column. Elongate rods are sometimes used to stabilize and support portions of the spinal column in an attempt to correct spinal deformities or curvatures relating to scoliosis or other conditions. In certain instances involving spinal disorders or degenerative conditions, the treatment techniques and systems are used in association with spinal fusion techniques to promote fusion between one or more pairs of adjacent vertebrae.

In some techniques and systems, elongate rods are positioned along opposite sides of the spinal column. The elongate rods are engaged to two or more vertebrae by way of a number of anchor elements, such as screws and/or hooks, to provide a spinal construct that functions to stabilize and support at least a portion of the spinal column. The overall structural integrity and stability of the spinal construct is sometimes enhanced by providing one or more transverse connectors that interconnect the elongate rods at one or more locations along the length of the rods. The transverse connectors link the rods together to prevent rod migration and to increase the overall stiffness of the spinal construct. In cases involving spinal fusion, the use of transverse connectors is particularly beneficial in stabilizing/stiffening the spinal construct to enhance or promote fusion between one or more pairs of adjacent vertebrae.

Many prior transverse connectors present one or more difficulties for spinal surgeons. For example, some prior transverse connectors have a relatively high profile which potentially increases soft tissue trauma and surgical complications. Additionally, some prior transverse connectors must be pre-loaded onto the elongate rods prior to implantation within the patient. Such preloading may require significant pre-operative planning and eliminates the opportunity to engage the transverse connectors to the elongate rods in situ. Further, adjusting the position of the transverse connectors during the surgical procedure can be difficult to accomplish.

Thus, there is a general need in the industry to provide an improved device for interconnecting components in spinal instrumentation. The present invention satisfies this need and provides other benefits and advantages in a novel and unobvious manner.

SUMMARY

The present invention relates generally to devices for interconnecting components in spinal instrumentation. While the actual nature of the invention covered herein can only be determined with reference to the claims appended hereto, certain forms of the invention that are characteristic of the preferred embodiments disclosed herein are described briefly as follows.

In one form of the present invention, a device is provided for connection to a component used in association with spinal instrumentation, including a connector body, a clamp element and a fixation element. The connector body defines a receptacle extending therethrough and opening onto an outer surface thereof, with the receptacle including a pair of oppositely facing tapered engagement surfaces. The connector body further defines a passage in transverse communication with the receptacle. The clamp element includes at least two arm portions defining a space therebetween having an open end. The clamp element is positioned within the passage in the connector body with the space between the arm portions generally aligned with the receptacle and with the component received through the open end and retained within the space. The fixation element interacts with the clamp element to displace the clamp element relative to the connector body to engage the component against the tapered engagement surfaces.

In another form of the present invention, a device is provided for connection to a component used in association with spinal instrumentation, including a connector body, a clamp element and a fixation element. The connector body defines a receptacle extending therethrough and opening onto an outer surface thereof. The connector body further defines a passage in transverse communication with the receptacle. The clamp element includes at least two arm portions defining a space therebetween having an open end, and is positioned within the passage in the connector body with the space generally aligned with the receptacle and with the component received through the open end and into the space. The connector body and the clamp element include anti-rotation features that cooperate with one another to substantially prevent rotation of the clamp element within the passage. Additionally, at least one of the connector body and the arm portions of the clamp element defines a tapered region. The fixation element interacts with the clamp element to displace the clamp element relative to the connector body along the tapered region to compress the arm portions about the component to retain the component within the space with the component at least partially positioned within the receptacle.

In another form of the present invention, a device is provided for connection to a component used in association with spinal instrumentation, including a connector body, a clamp element and a fixation element. The connector body defines a receptacle extending therethrough and opening onto an outer surface thereof. The connector body further defines a passage in transverse communication with the receptacle. The clamp element includes at least two arm portions defining a space therebetween having an open end, and also includes an upper portion positioned within the passage in the connector body and a lower portion positioned adjacent the receptacle with the space generally aligned with the receptacle and with the component received through the open end and into the space. The connector body and the upper portion of the clamp element include anti-rotation features that cooperate with one another to substantially prevent rotation of the clamp element within the passage. A fixation element interacts with the clamp element to displace the clamp element relative to the connector body and to position at least a portion of the component within the receptacle.

In another form of the present invention, a device is provided for connection to a component used in association with spinal instrumentation, including a connector body, a clamp element and a fixation element. The connector body defines a receptacle extending therethrough and opening onto an outer surface thereof. The connector body further defines a passage in transverse communication with the receptacle, and also defines an engagement surface positioned along the passage. The clamp element includes a base portion defining a threaded opening and at least two arm portions extending from the base portion and defining a space therebetween having an open end. The clamp element is positioned within the passage in the connector body with the space generally aligned with the receptacle and with the component received through the open end and retained within the space. The fixation element includes a threaded portion threadingly engaged within the threaded opening of the clamp element, with the threaded portion having an end surface positioned in abutment against the engagement surface of the connector body such that rotation of the fixation element correspondingly pulls the clamp element into the connector body to position at least a portion of the component within the receptacle.

It is one object of the present invention to provide an improved device for interconnecting components in spinal instrumentation. Further objects, features, advantages, benefits, and aspects of the present invention will become apparent from the drawings and description contained herein.

BRIEF DESCRIPTION OF THE DRAWINGS

FIG. 4 is a perspective view of a connector body according to one embodiment of the present invention for use in association with the connection device illustrated in FIG. 1.

FIG. 5 is a side view of the connector body illustrated in FIG. 4.

FIG. 6 is a top view of the connector body illustrated in FIG. 4.

FIG. 7 is an end view of the connector body illustrated in FIG. 4.

FIG. 8 is a cross-sectional view of the connector body illustrated in FIG. 4, as taken along line 8-8 of FIG. 6.

DESCRIPTION OF THE PREFERRED EMBODIMENTS

Figure 1:
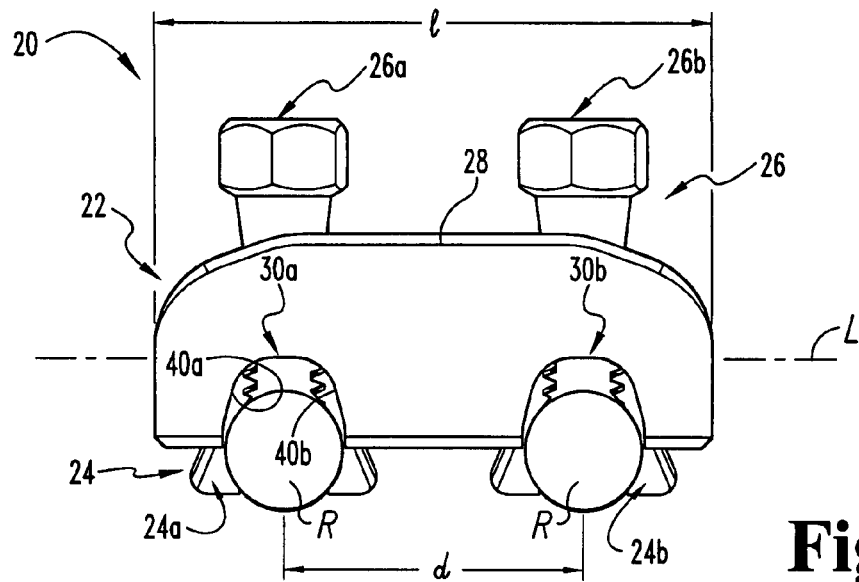
FIG. 1 is a side view of a connection device according to one form of the present invention for interconnecting a pair of elongate spinal rods.

For the purposes of promoting an understanding of the principles of the invention, reference will now be made to the embodiments illustrated in the drawings and specific language will be used to describe the same. It will nevertheless be understood that no limitation on the scope of the invention is hereby intended, and that alterations and further modifications in the illustrated devices, and further applications of the principles of the invention as illustrated herein are contemplated as would normally occur to one skilled in the art to which the invention relates.

Referring to FIG. 1, shown therein is a connection device 20 according to one form of the present invention for interconnecting components used in association with spinal instrumentation. In the illustrated embodiment, the connection device 20 is used to transversely connect a pair of elongate spinal rods R. The elongate spinal rods R are in turn attached to opposite sides of the spinal column by way of a number of anchor elements (not shown), such as screws or hooks, to form a spinal construct that stabilizes and supports the spinal column and, in some instances, serves to facilitate spinal fusion between one or more pairs of adjacent vertebrae.

In one embodiment of the invention, the spinal construct is attached to a posterior aspect of the spinal column. However, attachment of the spinal construct to other aspects or portions of the spinal column is also contemplated as falling within the scope of the present invention. The details regarding attachment of the elongate rods R to the spinal column are well known to those of skill in the art and therefore need not be specifically discussed herein. However, one example of the attachment of a pair of elongate rods to the spinal column is illustrated and described in U.S. Pat. No. 6,402,751 to Van Hoeck et al., the contents of which are incorporated herein by reference. Although the illustrated embodiment of the connection device 20 is used to interconnect a pair of elongate spinal rods R, it should be understood that connection devices according to other forms of the present invention may be used to interconnect other types of spinal instrumentation components. For example, connection devices according to other forms of the present invention may be used to interconnect a rod to a plate, a rod to a screw or hook, a rod to an implant, or any component or device associated with spinal constructs or assemblies to any other spinal component or device.

In one embodiment of the invention, the connection device 20 generally includes a connector body 22, one or more clamp elements or pincers 24, and one or more fixation elements or fasteners 26 configured to compress the clamp element 24 about a component used in association with spinal instrumentation. As indicated above, in the illustrated embodiment, the connection device 20 is used to transversely interconnect a pair of elongate spinal rods R. Accordingly, the connection device 20 includes a connector body 22, a pair of clamp elements 24a, 24b configured to receive respective ones of the spinal rods R therein, and a pair of fixation elements 26a, 26b configured to engage the clamp elements 24a, 24b about respective ones of the spinal rods R. However, as should be appreciated, connection devices according to other forms of the present invention may include a single clamp element and a corresponding fixation element, or three or more clamp elements and a corresponding number of fixation elements. Additionally, in the illustrated embodiment of the invention, the connection device 20 is configured to interconnect the spinal rods R in a substantially parallel configuration and a co-planar arrangement. However, in other embodiments, the connection device may be configured to interconnect the spinal rods in a non-parallel or oblique configuration and/or in a non-planar arrangement. Additionally, in the illustrated embodiment, the connection device 20 is configured to interconnect the spinal rods R in a manner wherein the distance d between the spinal rods R is fixed. However, in other embodiments, the connection device 20 may be configured to interconnect the spinal rods such that the distance d between the spinal rods R is variable or adjustable.

Figure 2:
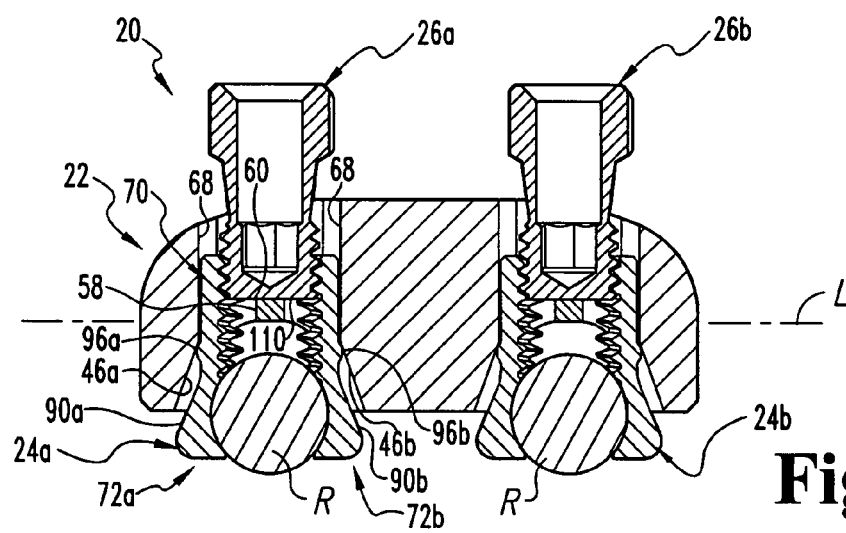
FIG. 2 is a side cross-sectional view of the connection device illustrated in FIG. 1, as shown in a first operational configuration.
Figure 3:
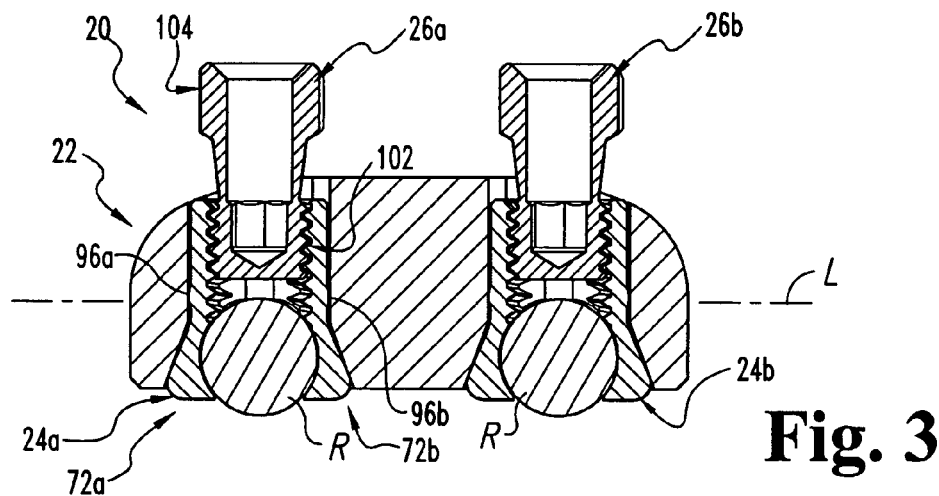
FIG. 3 is a side cross-sectional view of the connection device illustrated in FIG. 1, as shown in a second operational configuration.
Figure 9:
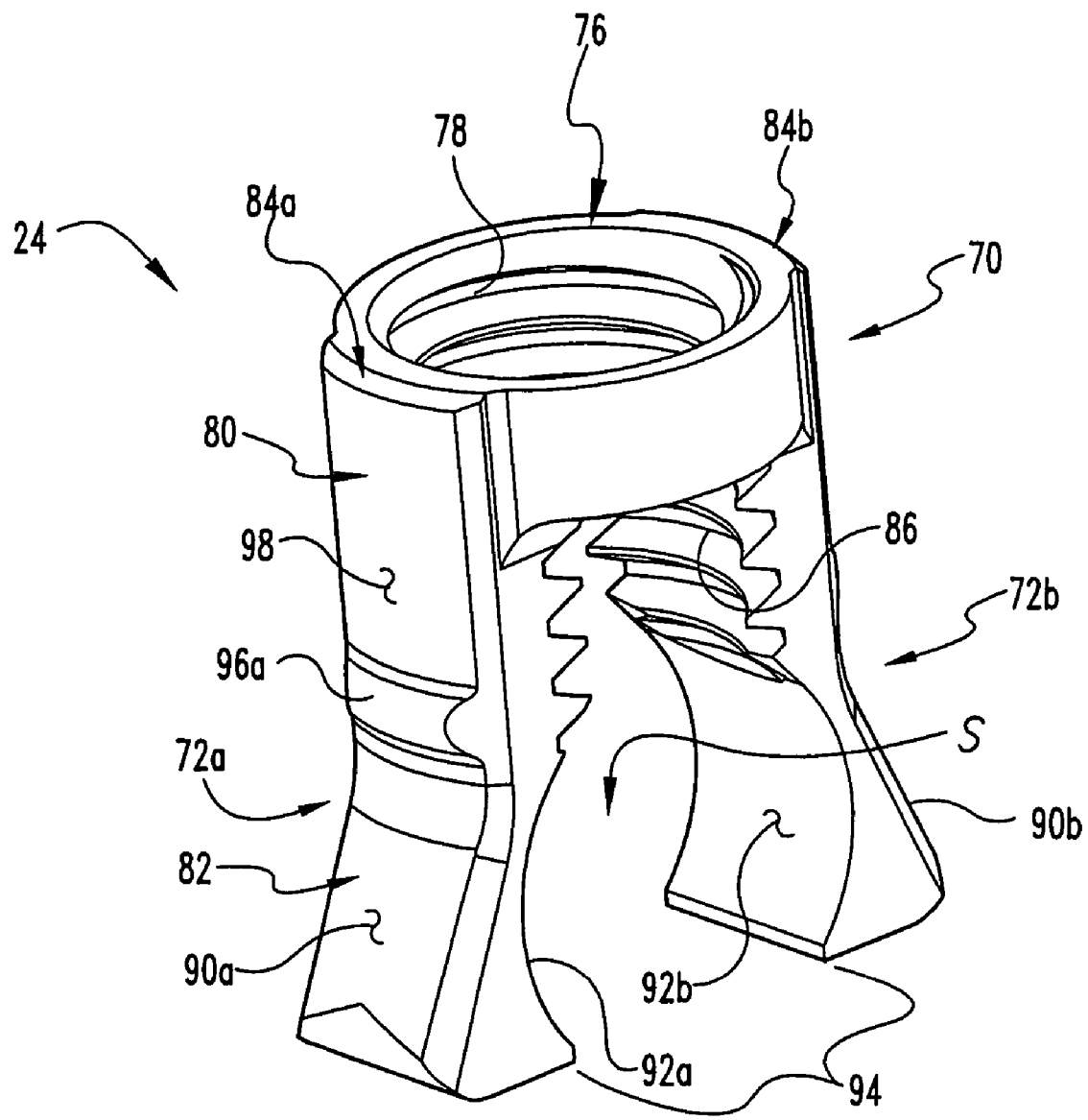
FIG. 9 is a perspective view of a clamp element according to one embodiment of the present invention for use in association with the connection device illustrated in FIG. 1.
Figure 11:
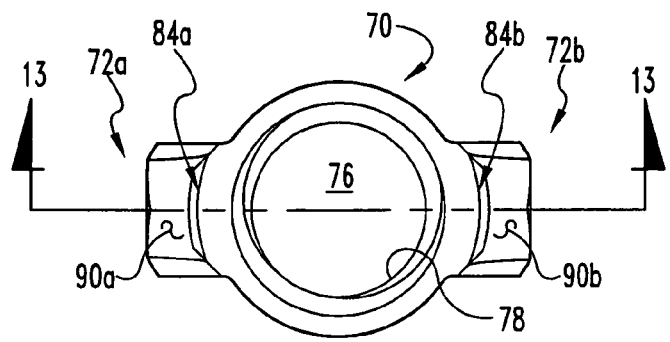
FIG. 11 is a top view of the clamp element illustrated in FIG. 9.
Figure 10:
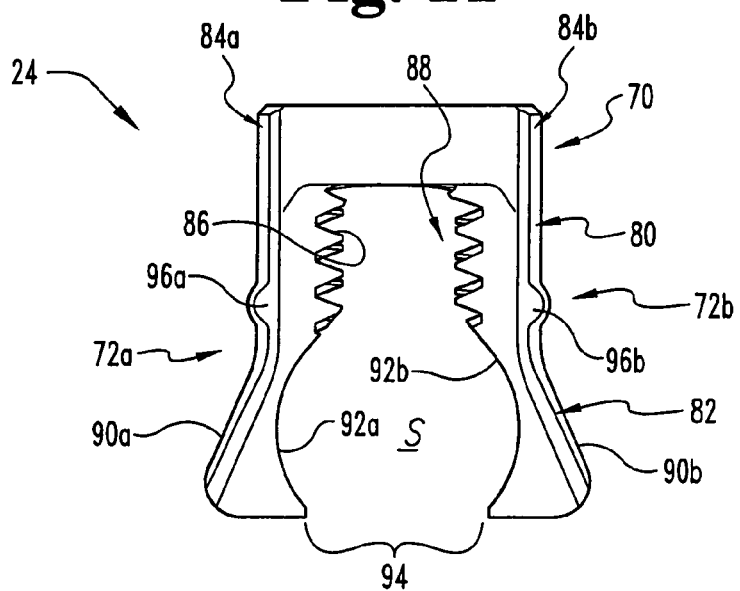
FIG. 10 is a side view of the clamp element illustrated in FIG. 9.
Figure 13:
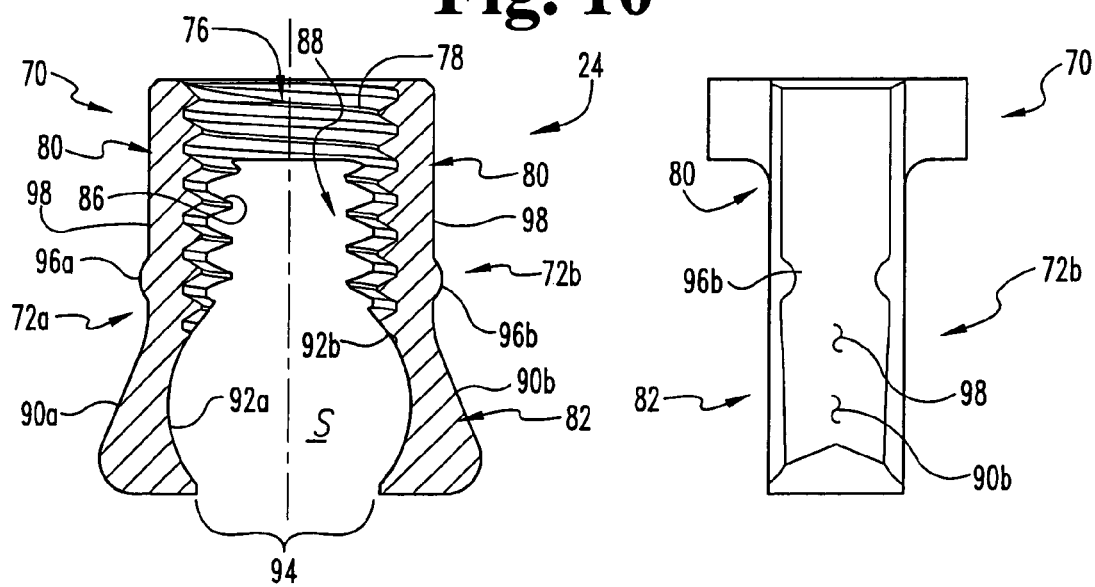
FIG. 13 is a cross-sectional view of the clamp element illustrated in FIG. 9, as taken along line 13-13 of FIG. 11.
Figure 12:
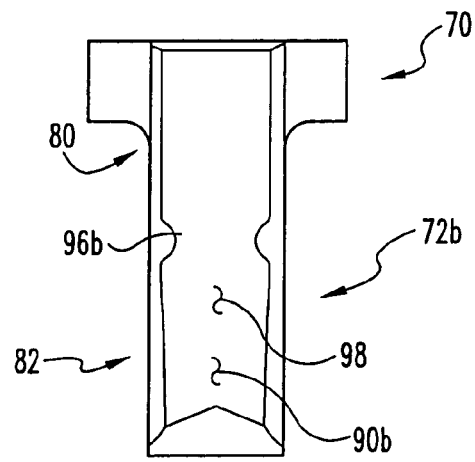
FIG. 12 is an end view of the clamp element illustrated in FIG. 9.

Referring to FIGS. 2 and 3, show therein is the connection device 20 in two distinct operational configurations. With reference to FIG. 2, the connection device 20 is shown in a first operational configuration wherein the clamp elements 24a, 24b are provisionally engaged to the spinal rods R in such a manner as to allow the connection device 20 to be displaced relative to the spinal rods R. In one embodiment, the connection device 20 is capable of being axially displaced along a length of the spinal rods R when in the first operational configuration illustrated in FIG. 2. Additionally, when in the first operational configuration, the connection device 20 is capable of being rotated about the longitudinal axis of one or both of the spinal rods R. As will be discussed further below, the clamp elements 24a, 24b are loosely engaged about the spinal rods R when in the first operational configuration. However, the clamp elements 24a, 24b are drawn toward the connector body 22 in response to engagement between the fixation elements 26a, 26b and the clamp elements 24a, 24b to transition the connection device 20 to the second operational configuration illustrated in FIG. 3. When transitioned toward the second operational configuration, the clamp elements 24a, 24b are compressed about the spinal rods R in a manner which securely engages the connection device 20 to the spinal rods R to substantially prevent displacement of the connection device 20 relative to the spinal rods R, the details of which will be discussed below.

Figure 16:
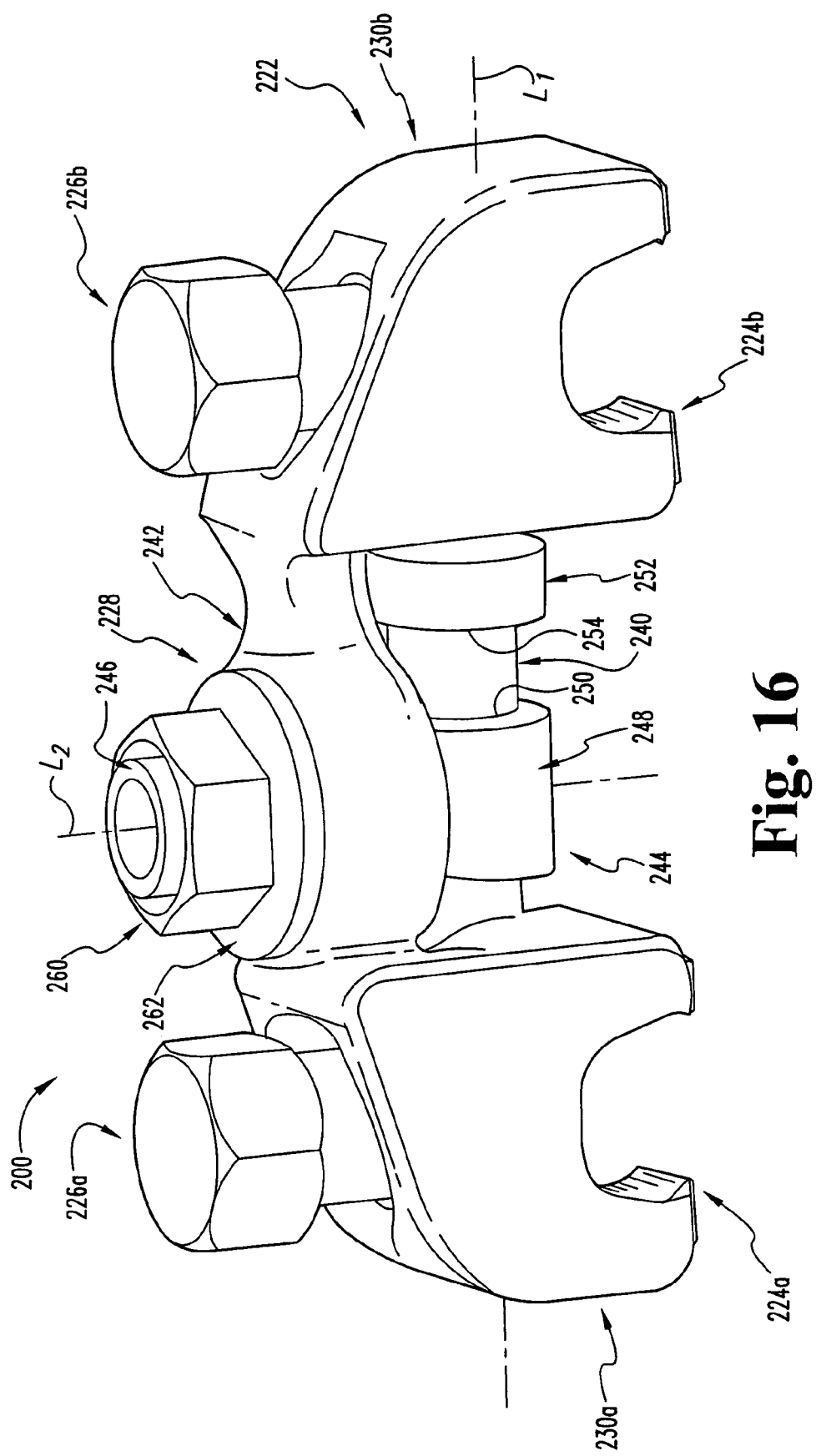
FIG. 16 is a perspective view of a connection device according to another form of the present invention for interconnecting a pair of elongate spinal rods.

In the illustrated embodiment of the invention, the bridge portion 28 of the connector body 22 is substantially rigid and non-adjustable. Accordingly, the connection device 20 has a non-adjustable length l to correspondingly interconnect the spinal rods R in a manner wherein the distance d between the spinal rods R is fixed. However, as will be discussed below with regard to FIG. 16, other embodiments of connection devices are also contemplated wherein the length of the connector body is adjustable such that the distance d between the spinal rods R is correspondingly adjustable. Additionally, as also illustrated in FIG. 16, connection devices are contemplated wherein the spinal rods R may be angulated relative to one another along a common plane and/or along different planes. Further embodiments of connection devices are also contemplated wherein the bridge portion of the connector body may include a region of reduced strength (such as a reduced cross sectional area) that allows for contouring or bending of the connector body as needed to conform to the spinal anatomy of the patient and/or to allow the spinal rods R to be angulated relative to one another along a common plane and/or along different planes.

Referring to FIGS. 4-8, shown there are further details regarding the connector body 22. In one embodiment, the connector body 22 is formed of a titanium alloy material such as, for example, Ti-6Al-4V. However, other materials are also contemplated, including titanium, stainless steel, or other materials know to those of skill in the art. In the illustrated embodiment, the connector body 22 has a generally rectangular configuration extending along a longitudinal axis L. The upper corner portions of the connector body 22 are rounded to prevent or at least minimize injury or trauma to adjacent tissue. The connector body 22 can be provided in different overall lengths l to accommodate for various distances d between the spinal rods R.

In the illustrated embodiment of the invention, the connector body 22 defines one or more receptacles 30 extending transversely across the width w of the connector body 22 between opposite side surfaces 32a, 32b. Each of the receptacles 30 defines an opening 34 adjacent a lower surface 36 of the connector body 22. The receptacles 30 and the openings 34 are each sized and configured to receive a spinal rod R therein. In the illustrated embodiment, the connector body 22 includes a pair of receptacles or channels 30a, 30b that are each sized and configured to receive respective ones of the pair of spinal rods R therein. However, as indicated above, other embodiments of connection devices are also contemplated which are configured for engagement with a single spinal rod R or three or more spinal rods R, in which case the connection device would define a single receptacle 30 or three or more receptacles 30.

Each of the receptacles 30 are defined by a pair of tapered side walls 40a, 40b that extend from the lower surface 36 of the connector body 22 to an upper surface 42. In one embodiment, the tapered side walls 40a, 40b define a taper angle therebetween of about 30 degrees; however, other taper angles are also contemplated as falling with the scope of the present invention. In the illustrated embodiment, the tapered side walls 40a, 40b transition into the upper surface 42 by way of arcuate or rounded surfaces 43a, 43b. However, it should be understood that other configurations of the receptacles 30 are also contemplated as falling within the scope of the present invention. The connector body 22 also defines an inner tapered region 44 (FIG. 8) adjacent each of the receptacles 30. The inner tapered region 44 does not extend the full width w of the connector body 22, but instead stops short of the side surfaces 32a, 32b. The inner tapered region 44 defines a pair of tapered engagement surfaces 46a, 46b that are outwardly offset in an axial direction relative to the tapered side walls 40a, 40b defined by the receptacles 30. In one embodiment, the tapered engagement surfaces 46a, 46b define a taper angle therebetween of about 40 degrees; however, other taper angles are also contemplated as falling with the scope of the present invention. The purpose of the tapered engagement surfaces 46a, 46b will be discussed below.

The connector body 22 further defines a passage 50 extending from the upper surface 38 of the connector body 22 and communicating with a respective one of the receptacles 30 and inner tapered regions 44. As indicated above, in the illustrated embodiment, the connector body 22 includes a pair of receptacles 30a, 30b, and therefore also includes a pair of passages 50a, 50b communication with respective ones of the receptacles 30a, 30b. Each of the passages 50a, 50b includes an upper portion 52 having a generally circular configuration; however, other shapes and configurations are also contemplated. Each of the passages 50a, 50b also includes a lower portion 54 defined by a pair of generally rectangular apertures 56a, 56b extending through an intermediate inner wall or bridge member 58. However, other shapes and configurations of the apertures 56a, 56b are also contemplated. The inner wall or bridge member 58 is generally disposed between the upper portion 52 of the passages 50a, 50b and the receptacles 30a, 30b, and defines an upwardly facing surface or shoulder 60. The upper portion 52 of the passages 50a, 50b further defines a pair of opposite recessed regions or channels 66a, 66b that are generally aligned with the apertures 56a, 56b extending through the bridge member 58. However, it should be understood that the recessed regions 66a, 66b need not necessarily be aligned with the apertures 56a, 56b, but may instead be angularly offset relative thereto. Each of the recessed regions 66a, 66b includes an outer wall 68 that is generally contiguous with the tapered engagement surfaces 46a, 46b.

Referring to FIGS. 9-13, shown there are further details regarding the clamp element 24. In one embodiment, the clamp element 24 is formed of a titanium alloy material such as, for example, Ti-6Al-4V. However, other materials are also contemplated, including titanium, stainless steel, plastic or polymeric materials, or other materials know to those of skill in the art. In the illustrated embodiment, the clamp element 24 includes a base portion 70 and a pair of opposite arm or pincer portions 72a, 72b extending from the base portion 70. The interconnection between the base portion 70 and the arms 72a, 72b is configured such that the arms 72a, 72b may be displaced toward and away from one another in such a manner as to allow the clamp element 24 to be positioned over and compressed or clamped about one of the spinal rods R.

In one embodiment, the arms 72a, 72b are flexibly connected to the base portion 70 such that the arms 72a, 72b may be inwardly and outwardly deflected relative to one another. However, other connection arrangements between the base 70 and the arms 72a, 72b are also contemplated as falling within the scope of the present invention. In the illustrated embodiment, the arms 72a, 72b are formed integral with the base portion 70 so as to define a unitary, single-piece clamp element 24. However, other embodiments are also contemplated wherein the arms 72a, 72b are formed separate from one another and subsequently connected to the base 70. For example, in one alternative embodiment, the arms 72a, 72b may be connected to the base 70 by a hinge or pivot pin.

In the illustrated embodiment of the invention, the base 70 has an annular ring-like configuration defining an outer profile sized and shaped to generally correspond to the inner profile of the upper portion 52 of the passages 50a, 50b in the connector body 22. As a result, the base 70 is receivable within and displaceable along the upper portion 52 of the passages 50a, 50b (FIGS. 2 and 3). The base 70 also defines an opening 76 extending therethrough in the general direction of the arms 72a, 72b. In one embodiment, the opening 76 defines internal threads 78 configured for engagement with external threads defined along an exterior surface of the fixation element 26, the function of which will be discussed below.

Each of the arms 72a, 72b includes an upper portion 80 extending from the base portion 70 and a lower portion 82 configured for engagement with one of the spinal rods R. The upper portions 80 of the arms 72a, 72b include projecting portions 84a, 84b that extend beyond the outer surface of the base portion 70. The projection portions 84a, 84b each have an outer profile that is sized and shaped to generally correspond to the inner profile of the recessed regions 66a, 66b defined by the passages 50a, 50b in the connector body 22. As a result, positioning of the projecting portions 84a, 84b within the recessed regions 66a, 66b substantially prevents the clamp element 24 from rotating relative to the connector body 22, while still permitting the clamp element 24 to be axially displaced along the passages 50a, 50b in the connector body 22. In one embodiment, the inner surfaces of the upper arm portions 80 define internal threads 86 that cooperate with the internal threads 78 defined by the base portion 70 to form a substantially continuing and uniform thread pattern 88 configured for engagement with external threads defined along an exterior surface of the fixation element 26, the function of which will be discussed below.

In the illustrated embodiment of the invention, the lower portions 82 of the arms 72a, 72b define outwardly facing tapered surfaces 90a, 90b that generally correspond to the tapered engagement surfaces 46a, 46b defined by the connector body 22. Additionally, the lower portions 82 of the arms 72a, 72b define inwardly facing curved surfaces 92a, 92b that generally correspond to the outer profile of the spinal rods R and which define a space S therebetween sized to receive one of the spinal rods R therein. Specifically, the inwardly facing curved surfaced 92a, 92b are each sized and configured for clamping engagement about the outer surface of the spinal rod R. The distal ends of the arms 72a, 72b are separated from one another to form an opening 94 sized somewhat smaller than the outer diameter of the spinal rods R. Additionally, the clamp elements 24a, 24b define a pair of surface protrusions 96a, 96b extending from an outer surface 98 of each of the arms 72a, 72b, the purpose of which will be discussed below.

Figures 14, 15:
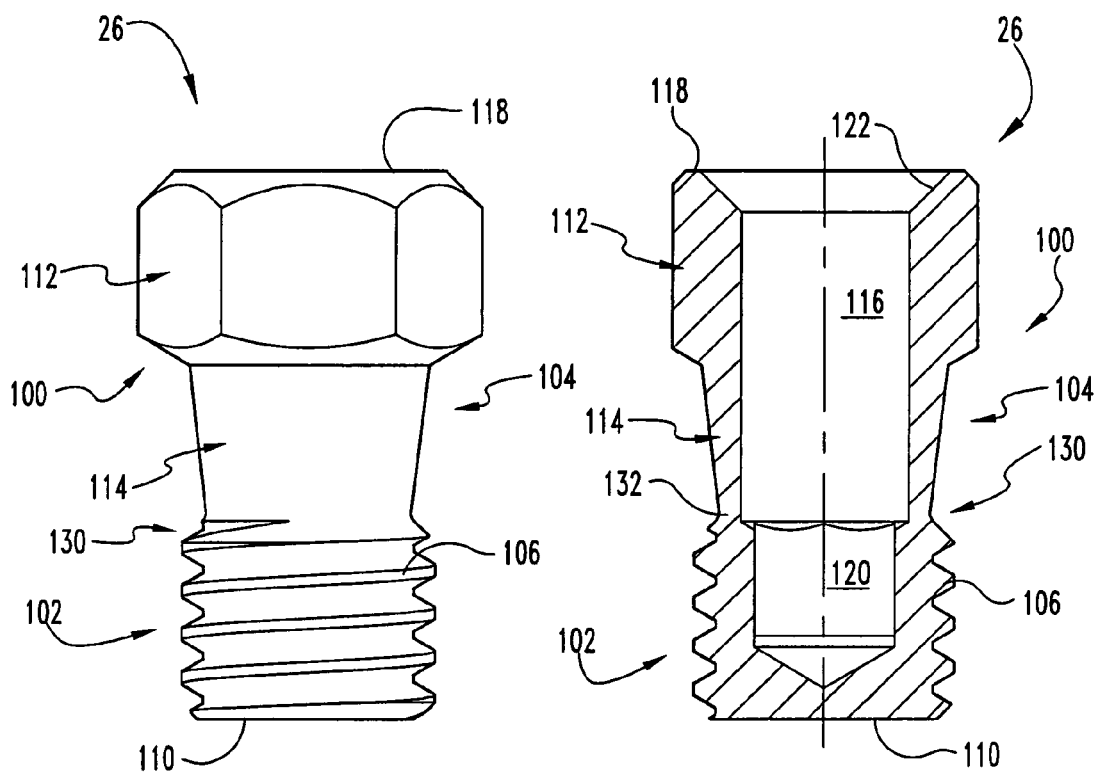
FIG. 14 is a side view of a fixation element according to one embodiment of the present invention for use in association with the connection device illustrated in FIG. 1.
FIG. 15 is a cross-sectional side view of the fixation element illustrated in FIG. 14.

Referring to FIGS. 14 and 15, shown there are further details regarding the fixation element 26. In one embodiment, the fixation element 26 is formed of a titanium alloy material such as, for example, Ti-6Al-4V. However, other materials are also contemplated, including titanium, stainless steel, or other materials know to those of skill in the art. As indicated above, the fixation element 26 is configured to engage the clamp elements 24a, 24b in a manner that results in compression of the clamp elements 24a, 24b about respective ones of the spinal rods R. In the illustrated embodiment of the invention, the fixation element 26 is configured as a fastener or setscrew 100. However, other types and configurations of fixation elements that are capable of compressing the clamp elements 24a, 24b about respective ones of the spinal rods R are also contemplated as falling within the scope of the invention.

In the illustrated embodiment of the invention, the setscrew 100 generally includes a body portion 102 and a head portion 104. The body portion 102 defines external threads 106 configured for threading engagement with the internal thread pattern 88 formed along the opening 76 in the base portion 70 of the clamp elements 24a, 24b and between the arms 72a, 72b. The body portion 102 also defines a lower end surface 110 having a substantially flat or planar configuration for engagement with the upper surface 60 of the bridge member 58 in the connector body 22.

In one embodiment, the head portion 104 of the setscrew 100 includes a hexagonal-shaped upper portion 112 and a tapered intermediate portion 114 extending between the upper portion 112 and the threaded body portion 102. The hexagonal-shaped upper portion 112 is configured for engagement with the end portion of a surgical instrument (not shown) to allow for selective removal of the head portion 104 of the setscrew 100 from the body portion 102. However, other shapes and configurations of the upper portion 112 and the intermediate portion 114 are also contemplated as would be apparent to one of skill in the art. A passage 116 extends from an upper surface 118 of the head portion 104 to a location adjacent the point of connection between the body portion 102 and the head portion 104. A tool engaging recess 120 is formed in the threaded body portion 102 in communication with the passage 116. The tool engaging recess 120 is sized and configured for engagement with a corresponding end portion of a driving tool (not shown) for application of a rotary driving force to the setscrew 100. In the illustrated embodiment, the tool engaging recess 120 has a hexagonal configuration sized to receive a hexagonal-shaped end portion of a driving tool therein. However, other shapes and configurations of the tool engaging recess 120 are also contemplated as would be apparent to one of skill in the art. The upper portion of the passage 116 adjacent the upper surface 118 defines a chamfer 122 to facilitate insertion of the end portion of a driving tool therein.

In the illustrated embodiment of the invention, the head portion 104 of the setscrew 100 is removably attached to the body portion 102 in such a manner as to allow selective separation of the head portion 104. In the illustrated embodiment, the head portion 104 is attached to the body portion 102 by a region of reduced strength 130 to allow the head portion 104 to be fractured or broken off from the body portion 102. In a specific embodiment, the region of reduced strength 130 is formed by a reduced cross-sectional area 132 adjacent the connection location between the body portion 102 and the head portion 104. As shown in FIG. 15, the reduced cross-section area 132 is formed by a reduction in the outer cross section defined by the inwardly tapering intermediate portion 114 in combination with the relatively large inner cross section of the passage 116 (compared to that of the tool-engaging recess 120) adjacent the point of connection between the body portion 102 and the head portion 104. As should be appreciated, application of a select amount of rotational torque to the head portion 104 of the setscrew 100 will cause the intermediate portion 114 to fracture adjacent the region of reduced cross-sectional area 132 so as to allow for the selective removal of the head portion 104 from the body portion 102. As should be further appreciated, removal of the head portion 104 from the remainder of the setscrew 100 results in a lower overall profile height of the connection device 20. Additionally, the body portion 102 is preferably positioned entirely below the upper surface 38 of the connector body 22 subsequent to removal of the head portion 104, thereby reducing the risk of injury or trauma to adjacent tissue.

Although a specific configuration of the setscrew 100 has been illustrated and described herein, it should be understood that other types and configurations of setscrews are also contemplated. For example, other features for allowing selective removal of the head portion 104 from the body portion 102 are also contemplated as falling within the scope of the invention. Additionally, in other embodiments of the invention, the head portion 104 need not be configured for selective removal from the body portion 102. In still other embodiments, the setscrew 100 need not necessarily include a head portion 104, but may instead include only the threaded body portion 102.

Having illustrated and described various structural and functional features associated with the components of the connection device 20, reference will now be made to the assembly and use of the connection device 20 according to one embodiment of the present invention. Referring collectively to FIGS. 1-15, in one embodiment of the invention, the components of the connection device 20 are preassembled prior to commencement of the surgical procedure. As a result, the surgeon may simply select an appropriate connection device 20 having a connector body 22 sized and configured to interconnect the spinal rods R such that the spinal rods R are separated by a distance d.

In one embodiment, the clamp elements or pincers 24a, 24b are initially assembled with the connector body 22 by slightly compressing the arms 72a, 72b toward one another and introducing the end portions of the arms 72a, 72b through the apertures 56a, 56b in the bridge member 58 of the connector body 22, with the projecting portions 84a, 84b of the arms 72a, 72b positioned within the recessed regions 66a, 66b defined by the passages 50a, 50b in the connector body 22. Since the outer cross-sectional dimension of the clamp elements 24a, 24b adjacent the surface protrusions 96a, 96b is slightly greater than the inner dimension between the outer walls 68 of the recessed regions 66a, 66b in the connector body 22, additional inward deflection of the arms 72a, 72b takes place during insertion of the clamp elements 24a, 24b through the upper portions 52 of passages 50a, 50b in the connector body 22. However, as the clamp elements 24a, 24b are further displaced through the passages 50a, 50b in the connector body 22, the arms 72a, 72b will resiliently spring back to their uncompressed, original configuration. As indicated above, positioning of the projecting portions 84a, 84b of the clamp arms 72a, 72b within the recessed regions 66a, 66b of the connector body 22 substantially prevents rotational movement of the clamp elements 24a, 24b relative to the connector body 22 while still allowing for axial displacement of the clamp elements 24a, 24b along the passages 50a, 50b in the connector body 22.

When the clamp elements 24a, 24b are fully inserted through the passages 50a, 50b in the connector body 22, the base portion 70 rests against the bridge 58 of the connector body 22, with the surface protrusions 96a, 96b positioned just beyond the outer walls 68 of the recessed regions 66a, 66b adjacent the upper end portions of the tapered engagement surfaces 46a, 46b. In this initial position, the clamp elements 24a, 24b are provisionally engaged to the connector body 22 in a manner that prevents the clamp element 24a, 24b from inadvertently falling out of the passages 50a, 50b. Following assembly of the clamp elements 24a, 24b with the connector body 22, the threaded body portions 102 of the setscrews 100 are threaded into the openings 76 in the base portion 70 of the clamp elements 24a, 24b until the lower end surface 110 of the setscrew 100 is positioned adjacent the upper surface 60 of the bridge member 58. The initial assembled configuration of the connection device 20 is illustrated in FIG. 2.

Once assembled to the configuration illustrated in FIG. 2, the connection device 20 may be provisionally engaged to the spinal rods R. In one embodiment of the invention, the rods R are anchored to the spinal column prior to engagement of the connection device 20 to the spinal rods R. However, it is also contemplated that the connection device 20 may be engaged to the spinal rods R prior to anchoring of the rods R to the spinal column. Notably, the configuration of the connection device 20 allows the connection device 20 to be top loaded onto the spinal rods R subsequent to anchoring of the rods R to the spinal column. This tends to simply the surgical procedure and potentially reduces the required size of the surgical incision and resulting trauma to the patient.

Prior to engagement of the clamp elements 24a, 24b to the spinal rods R, the setscrews 100 may have to be slightly backed out of the threaded opening 76 in the base 70 to allow the arms 72a, 72b to be spread apart a sufficient distance to receive a spinal rod R through the end opening 94 and into the space S. With the receptacles 30a, 30b of the connector body 22 and the openings 94 of the clamp elements 24a, 24b aligned above respective ones of the spinal rods R, the surgeon presses down on the connection device 20 (such as by pushing down on the fixation elements 26a, 26b) with a force sufficient to spread the clamp arms 72a, 72b apart a sufficient distance such that the spinal rods R are transversely received through the end openings 94 and into the spaces S.

As shown in FIG. 2, due to the resilient nature of the clamp elements 24a, 24b, once the spinal rods R are positioned within the spaces S between the arms 72a, 72b, the arms 72a, 72b will snap back to their original, undeformed configuration, thereby provisionally capturing the spinal rods R between the arms 72a, 72b and provisionally engaging the connection device 20 to the rods R. However, when positioned in this first operational configuration, the clamp elements 24a, 24b are loosely engaged about the spinal rods R, thereby allowing the connection device 20 to be axially displaced along a length of the spinal rods R and/or rotated about the longitudinal axis of one or both of the spinal rods R without having to disengage the connection device 20 from the spinal rods R. Such displacement capabilities may be particularly advantageous during compression and/or distraction of the anchor elements (e.g., bone screws or hooks) that are used to anchor the rods R to the spinal column.

Once the connection device 20 is positioned at the proper location along the spinal rods R, the fixation elements 26a, 26b are employed to compress the clamp elements 24a, 24b about the spinal rods R. Specifically, the setscrews 100 are threaded along the threaded opening 76 in the base portion 70 of the clamp elements 24a, 24b until the lower end surface 110 of the setscrew 100 engages the upper surface 60 of the bridge member 58 in the connector body 22. As should be appreciated, further tightening of the setscrews 100 results in the clamp elements 24a, 24b being drawn up into the connector body 22. Specifically, continued threading engagement of the setscrews 100 through the threaded opening 76 in the base portion 70 and along the internal threads 86 of the arms 72a, 72b results in upward displacement of the clamp elements 24a, 24b along the passages 50a, 50b in the connector body 22. As indicated above, the outer cross-sectional dimension of the clamp elements 24a, 24b adjacent the surface protrusions 96a, 96b is slightly greater than the inner dimension between the outer walls 68 of the recessed regions 66a, 66b in the connector body 22. Accordingly, displacement of the surface protrusions 96a, 96b along the outer walls 68 of the recessed regions 66a, 66b results in inward deflection of the clamp arms 72a, 72b toward one another, which in turn results in initial compression of the clamp arms 72a, 72b about the circumference of the spinal rods R.

Upward displacement of the clamp elements 24a, 24b into the connector body 22 also results in upward displacement of the spinal rods R through the lower openings 34 in the connector body 22 and into the receptacles 30. Further tightening of the setscrews 100 engages the spinal rods R tightly against the tapered side walls 40a, 40b of the receptacles 30, thereby resulting in two points of contact between the connector body 22 and each of the spinal rods R. Further tightening of the setscrews 100 also results in sliding engagement between the outer tapered surfaces 90a, 90b of the clamp arms 72a, 72b and the inner tapered engagement surfaces 46a, 46b of the connector body 22. Sliding engagement between the outer tapered surfaces 90a, 90b and the inner tapered engagement surfaces 46a, 46b results in displacement of the clamp arms 72a, 72b toward one another, which in turn results in compression of the curved surfaces 92a, 93b of the clamp arms 72a, 72b tightly about the circumference of the spinal rods R, thereby resulting in two surface contacts between each of the clamp elements 24a, 24b and the spinal rods R. Once the connection device 20 is transitioned to the operational configuration shown in FIG. 3, with the connection device 20 securely engaged to the spinal rods R, the head portions 104 of the setscrews 100 may be broken away and selectively removed from the body portion 102, thereby providing the connection device 20 with a lower overall vertical profile.

As should be appreciated, engagement of the spinal rods R against the tapered side walls 40a, 40b of the receptacles 30 and compression of the clamp elements 24a, 24b tightly about the spinal rods R securely locks the connection device 20 to the spinal rods R, thereby substantially preventing further axial displacement of the connection device 20 along the length of the rods R and further rotational displacement of the connection device 20 about the longitudinal axis of the rods R. The connection device 20 interconnects the spinal rods R to prevent rod migration and to increase the overall stiffness and stability of the spinal construct. In cases involving spinal fusion, the connection device 20 is particularly beneficial to enhance or promote fusion between one or more pairs of adjacent vertebrae. As show in FIG. 3, no portion of the connection device 20 extends below the spinal rods R, thereby allowing for placement of a greater amount of bone graft or other components or devices directly beneath the connection device 20. Additionally, the relatively low vertical profile of the connection device 20 minimizes the risk of injury or trauma to adjacent tissue. In one embodiment of the invention, a pair of connection devices 20 is used to interconnect the spinal rods R. However, it should be appreciated that in other embodiments, a single connection device 20 or three or more connection devices 20 may be used to interconnect the spinal rods R.

Referring to FIG. 16, shown therein is a connection device 200 according to another form of the present invention for interconnecting spinal instrumentation components. Similar to the connection device 20 illustrated and described above, the connection device 200 is configured to transversely interconnect a pair of elongate spinal rods R (not shown). The elongate rods R are in turn attached to opposite sides of the spinal column by way of a number of anchor elements (not shown), such as screws or hooks, to form a spinal construct that stabilizes and supports the spinal column and, in some instances, serving to facilitate spinal fusion between one or more pairs of adjacent vertebrae. However, unlike the connection device 20 which is configured to interconnect the spinal rods R in a substantially parallel configuration and in a co-planar arrangement, the connection device 200 is adapted to variably interconnect the spinal rods R in a non-parallel or oblique configuration and/or in a non-planar arrangement. Additionally, unlike the connection device 20 which is configured to interconnect the spinal rods R in a manner wherein the distance between the rods R is fixed, the connection device 200 is adapted to interconnect the spinal rods R in a manner wherein the distance between the spinal rods is variable or adjustable.

In the illustrated embodiment, the connection device 200 generally includes a connector body 222, a pair of clamp elements or pincers 224a, 224b, and a pair of fixation elements or fasteners 226a, 226b that are configured to compress the clamp elements 224a, 224b about the spinal rods to securely engage the connection device 200 to the spinal rods. In one embodiment of the invention, the clamp elements 224a, 224b are configured substantially identical to the clamp elements 24a, 24b, and the fixation elements 226a, 226b are configured substantially identical to the fixation elements 26a, 26b. Additionally, the portions of the connector body 222 that interact and cooperate with the clamp elements 224a, 224b and the fixation elements 226a, 226b to engage the connection device 200 to the spinal rods are configured substantially identical to the corresponding portions of the connector body 22. As a result, the operation of the connection device 200 with regard to engagement of the device to the spinal rods is substantially identical to that of the connection device 20. Therefore, these features and operations need not be discussed again with regard to the connection device 200. However, unlike the non-adjustable bridge portion 28 associated with the connector body 22, the connector body 222 includes an adjustable bridge portion 228 that is configured to selectively vary the distance and the angular relationship between the spinal rods, the details of which will be discussed below.

In the illustrated embodiment of the invention, the connector body 222 includes a first receiver portion 230a that interacts and cooperates with the clamp element 224a and the fixation element 226a for engagement with a first spinal rod. Additionally, the connector body 222 includes a second receiver portion 230b that interacts and cooperates with the clamp element 224b and the fixation element 226b for engagement with a second spinal rod. The bridge portion 228 couples the first and second receiver portions 230a, 230b together in such a manner as to allow relative linear displacement between the receiver portions 230a, 230b along a first axis $L_1$ to correspondingly adjust the distance between the first and second spinal rods. Additionally, the bridge portion 228 allows angular displacement between the receiver portions 230a, 230b relative to the first axis $L_1$ to correspondingly adjust the angular relationship between the first and second spinal rods relative to a first plane. Further, the bridge portion 228 allows angular displacement between the receiver portions 230a, 230b relative to a second axis $L_2$ arranged transverse to the first axis $L_1$ to correspondingly adjust the angular relationship between the first and second spinal rods relative to a second plane arranged transverse to the first plane. In the illustrated embodiment, the first axis $L_1$ is substantially perpendicular to the second axis $L_2$.

In one embodiment, the bridge portion 228 includes a stud member 240 extending from the first receiver portion 230a and arranged generally along the first axis $L_1$, and a ring member 242 extending from the second receiver portion 230b and including a through opening (not shown) positioned generally along the second axis $L_2$. However, it should be understood that the positions of the stud member 240 and the ring member 242 may be reversed such that the stud member 240 extends from the second receiver portion 230b and the ring member 242 extends from the first receiver portion 230a. The bridge portion 228 further includes a coupling member 244 including a threaded stem portion 246 extending generally along the second axis $L_2$ and positioned within the through opening in the ring member 242, and a collar portion 248 including a through opening 250 which receives the stud member 240 therein.

As should be appreciated, the distance between the first and second spinal rods may be adjusted via linear displacement of the collar portion 248 of the coupling member 244 along the stud member 240 (i.e., along the first axis $L_1$). The end of the stud member 240 includes an enlarged portion 252 defining a shoulder 254 that prevents the collar portion 248 from sliding off of and disengaging the stud member 240. As should also be appreciated, the angular relationship between the first and second spinal rods may be adjusted via rotation of the collar portion 248 about the stud member 240 (i.e., about the first axis $L_1$). A setscrew (not shown) may be driven through a threaded aperture in the collar portion 248 and into engagement with the stud member 240 to prevent further linear displacement along the first axis $L_1$ and further rotational displacement about the first axis $L_1$. As should further be appreciated, the angular relationship between the first and second spinal rods may be adjusted via rotation of the ring member 242 about the stem portion 246 of the coupling member 244 (i.e., about the second axis $L_2$). A nut 260 is threaded onto the threaded stem portion 246 of the coupling member 244 and into engagement against a washer 262, which is in turn engaged against a surface of the ring member 242 to prevent further rotational displacement about the second axis $L_2$. As should now be appreciated, the connection device 200 is configured to allow selective adjustment of the distance between the first and second spinal rods and selective adjustment of the angular relationship between the first and second spinal rods relative to two axes of rotation. The bridge portion 228 also includes features for locking the first and second receiver portions 230a, 230b a select distance apart and at a select angular orientation relative to one another to correspondingly interconnect the first and second spinal rods a select distance apart and at a select angular orientation relative to one another.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A device used in association with spinal instrumentation, comprising:

a component used in association with spinal instrumentation;

a connector body defining a receptacle extending therethrough and opening onto an outer surface thereof, said receptacle including a pair of oppositely facing tapered engagement surfaces defining an inner dimension that is measured from one of the tapered engagement surfaces to another of the tapered engagement surfaces, said inner dimension is less than an outer dimension of the component and with no more than two points of direct contact defined between the component and said tapered engagement surfaces of said connector body, said connector body defining a passage in transverse communication with said receptacle;

a clamp element including at least two flexible arm portions flexibly interconnected to one another such that the arm portions may be inwardly and outwardly deflected relative to one another and defining a space therebetween having an open end, said clamp element positioned within said passage in said connector body with said space generally aligned with said receptacle and with the component received through said open end and retained within said space by compressing engagement of said at least two flexible arm portions about the component; and a fixation element interacting with said clamp element to displace said clamp element relative to said connector body, the component directly engaged against said tapered engagement surfaces at said no more than two points of direct contact including a first point of direct contact between the component and a first of said tapered engagement surfaces and a second point of direct contact between the component and a second of said tapered engagement surfaces to establish said no more than two points of direct contact between the component and said connector body.

2. The device of claim 1, wherein said connector body and said clamp element include anti-rotation features that cooperate with one another to substantially prevent rotation of said clamp element within said passage.

3. The device of claim 2, wherein said clamp element includes an upper portion positioned within said passage in said connector body and a lower portion positioned adjacent said receptacle, said anti-rotation features located adjacent said upper portion of said clamp element.

4. The device of claim 1, wherein at least one of said connector body and said arm portions of said clamp element defines a tapered region, said fixation element interacting with said clamp element to displace said clamp element relative to said connector body along said tapered region to compress said arm portions about the component.

5. The device of claim 4, wherein said tapered region is located proximately adjacent said receptacle.

6. The device of claim 1, wherein said connector body defines an engagement surface positioned along said passage, said clamp element including a base portion defining a threaded opening with said arm portions extending from said base portion, said fixation element including a threaded portion threadingly engaged within said threaded opening of said clamp element, said threaded portion disposed within said threading opening of said clamp element and having a leading end surface positioned in abutment against said engagement surface of said connector body such that rotation of said fixation element correspondingly pulls said clamp element into said connector body to position at least a portion of the component within said receptacle.

7. The device of claim 6, wherein said engagement surface is defined by an inner wall extending transversely across at least a portion of said passage.

8. The device of claim 7, wherein said inner wall defines at least two apertures sized to receive respective ones of said at least two arm portions therethrough.

9. The device of claim 6, wherein said engagement surface is defined by a bridge portion extending across said passage.

10. The device of claim 1, wherein said connector device comprises a first receiver portion, a second receiver portion, and a bridge portion extending between said first and second receiver portions, said first and second receiver portions each including one of said connector body, one of said clamp element, and one of said fixation element, each of said first and second receiver portions configured for connection to respective ones of first and second spinal rods.

11. The device of claim 10, wherein said bridge portion is configured to provide selective adjustment of a distance between said first and second spinal rods.

12. The device of claim 10, wherein said bridge portion is configured to allow selective adjustment of an angle between said first and second spinal rods.

13. The device of claim 1, wherein said fixation element comprises a setscrew including a threaded stem portion threadingly engaged within a threaded opening in said clamp element to displace said clamp element relative to said connector body.

14. The device of claim 13, wherein said setscrew includes a head portion selectively separable from said threaded stem portion.

15. The device of claim 1, wherein said clamp element includes an upper portion positioned within said passage in said connector body and a lower portion defining said space and positioned adjacent said receptacle; and further comprising anti-rotation features extending along said passage and said upper portion of said clamp element that cooperate with one another to substantially prevent rotation of said clamp element within said passage while permitting said clamp element to be axially displaced along said passage, wherein said anti-rotation features comprise a projection positioned within a groove.

16. The device of claim 15, wherein said projection extends along said upper portion of said clamp element and wherein said groove extends along said passage in said connector body.

17. The device of claim 15, wherein at least one of said connector body and said arm portions of said clamp element defines a tapered region, said fixation element interacting with said clamp element to displace said clamp element relative to said connector body along said tapered region to compress said arm portions about the component.

18. The device of claim 15, wherein said connector body defines an internal engagement surface positioned within said passage, said upper portion of said clamp element defining a threaded opening with said arm portions extending from said upper portion, said fixation element including a threaded portion threadingly engaged within said threaded opening of said clamp element, said threaded portion disposed within said threading opening of said clamp element and having a leading end surface positioned in abutment against said internal engagement surface of said connector body such that rotation of said fixation element correspondingly pulls said clamp element into said connector body to position at least a portion of the component within said receptacle.

19. The device of claim 18, wherein said engagement surface is defined by an inner wall extending transversely across at least a portion of said passage.

20. The device of claim 15, wherein said upper portion of said clamp element defines a threaded opening, said fixation element including a threaded portion threadingly engaged within said threaded opening such that rotation of said fixation element correspondingly pulls said clamp element into said connector body to position at least a portion of the component within said receptacle.

21. The device of claim 20, wherein said upper portion of said clamp element comprises a cylindrical portion at least partially defining said threaded opening.

22. The device of claim 21, wherein said projection and said groove extend axially along said cylindrical portion of said clamp element.

23. The device of claim 20, wherein said projection and said groove extend axially along said threaded opening in said upper portion of said clamp element.

24. A device for connection to a component used in association with spinal instrumentation, comprising:
   a connector body defining a receptacle extending therethrough and opening onto an outer surface thereof, said connector body defining a passage in transverse communication with said receptacle, said connector body including an inner wall positioned within and extending transversely across at least a portion of said passage, said inner wall including a bridge portion defining an internal engagement surface positioned within said passage with an aperture arranged on each side of said bridge portion;
   a clamp element including a base portion comprising an annular ring defining a threaded opening and at least two arm portions extending from said base portion and defining a space therebetween having an open end, said clamp element positioned within said passage in said connector body with said arm portions extending through said apertures and said annular ring resting on said bridge portion to provisionally maintain said clamp element within said passage of said connector body, and with said space generally aligned with said receptacle and the component received through said open end and retained within said space; and
   a fixation element including a threaded stem portion threadingly engaged within said threaded opening of said annular ring and having a leading end surface positioned in abutment against said engagement surface of said bridge portion such that rotation of said fixation element correspondingly pulls said clamp element into said connector body to position at least a portion of the component within said receptacle.

25. The device of claim 24, wherein said receptacle includes a pair of oppositely facing tapered engagement surfaces, said fixation element interacting with said clamp element to displace said clamp element relative to said connector body to engage the component against said tapered engagement surfaces.

26. The device of claim 24, wherein said connector body and said clamp element include anti-rotation features that cooperate with one another to substantially prevent rotation of said clamp element within said passage.

27. The device of claim 26, wherein said clamp element includes an upper portion positioned within said passage in said connector body and a lower portion positioned adjacent said receptacle, said anti-rotation features located adjacent said upper portion of said clamp element.

28. The device of claim 24, wherein at least one of said connector body and said arm portions of said clamp element defines a tapered region, said fixation element interacting with said clamp element to displace said clamp element relative to said connector body along said tapered region to compress said arm portions about the component.

29. The device of claim 24, wherein said bridge portion extends entirely across said passage.

30. The device of claim 24, wherein said fixation element comprises a setscrew including a head portion selectively separable from said threaded stem portion.

* * * * *